United States Patent [19]

Jinks et al.

[11] Patent Number: 4,814,161
[45] Date of Patent: Mar. 21, 1989

[54] DRUG-CONTAINING CHLOROFLUOROCARBON AEROSOL PROPELLENT FORMULATIONS

[75] Inventors: Philip A. Jinks, Mountsorrel; Alexander Bell, Chilwell, both of Great Britain; Franz X. Fischer, Riehen, Switzerland

[73] Assignee: Riker Laboratories, Inc., St. Paul, Minn.

[21] Appl. No.: 915,971

[22] PCT Filed: Jan. 2, 1986

[86] PCT No.: PCT/GB86/00001
§ 371 Date: Nov. 10, 1986
§ 102(e) Date: Nov. 10, 1986

[87] PCT Pub. No.: WO86/04233
PCT Pub. Date: Jul. 31, 1986

[30] Foreign Application Priority Data

Jan. 16, 1985 [GB] United Kingdom ............... 8501015

[51] Int. Cl.⁴ ............................................. A61K 31/00
[52] U.S. Cl. ......................................... 424/45; 514/78; 514/95; 514/99; 514/149; 514/183; 514/255; 514/315; 514/506; 514/558; 514/740; 514/743; 514/762; 514/767; 514/786; 514/937
[58] Field of Search ...................... 424/45; 514/78, 95, 514/99, 149, 241, 183, 255, 315, 506, 558, 762, 740, 743, 767, 786, 937

[56] References Cited

U.S. PATENT DOCUMENTS

| | | | |
|---|---|---|---|
| 4,310,526 | 1/1982 | Doria et al. | 514/258 |
| 4,380,534 | 4/1983 | Fukui et al. | 424/498 |
| 4,419,352 | 12/1983 | Cox et al. | 514/291 |

FOREIGN PATENT DOCUMENTS

| | | |
|---|---|---|
| 0993702 | 6/1965 | United Kingdom . |
| 2001334 | 1/1979 | United Kingdom . |

*Primary Examiner*—Morton Foelak
*Assistant Examiner*—S. A. Acquah
*Attorney, Agent, or Firm*—Donald M. Sell; Walter N. Kirn; Robert W. Sprague

[57] ABSTRACT

Complete dissolution of a wide range of drugs in chlorofluorocarbon aerosol propellents is achieved by the presence of glycerol phosphatides, preferably phosphatidylcholine.

16 Claims, No Drawings

DRUG-CONTAINING CHLOROFLUOROCARBON AEROSOL PROPELLENT FORMULATIONS

This invention relates to medicinal aerosol formulations and in particular to drug-containing chlorofluorocarbon aerosol propellent formulations for topical or for endopulmonary or nasal inhalation administration.

Medicinal aerosol formulations generally contain a mixture of chlorofluorocarbons, e.g. trichloromonofluoromethane (Propellent 11), dichlorotetrafluoroethane (Propellent 114) and dichlorodifluoromethane (Propellent 12). The drug is either present as a solution in the aerosol formulation or as a dispersion of fine particles. For endopulmonary or nasal inhalation, particles predominantly in the size range 2 to 5 microns are required.

There are very few drugs which can be solubilised in chlorofluorocarbon aerosol propellents alone. Generally, it is necessary to utilise a polar co-solvent, such as ethanol, in order to achieve solubilisation of the drug. However, the resulting solutions can be chemically unstable due to reaction between the co-solvent and the drug or the co-solvent and the propellent system.

Furthermore, when large proportions of co-solvent, e.g. ethanol, are required to achieve dissolution of the drug, the resulting spray droplet size may be too large for certain applications, in particular, endopulmonary inhalation therapy.

Suspension of drug in aerosol propellents is achieved by pulverising the drug into the desired particle size range and thereafter suspending the particles in propellents with the aid of a surfactant. The disadvantages of this technique are that drug particles may agglomerate, grow in size or become adsorbed onto the surface of the container in which the formulations are stored prior to dispensing. Furthermore, it is necessary to agitate the product prior to use in order to ensure dispersion of the formulation and uniformity of dosage.

The present invention provides an alternative technique for incorporating drugs into chlorofluorocarbon aerosol propellents.

Therefore according to the invention there is provided an aerosol formulation comprising one or more chlorofluorocarbon aerosol propellents, a glycerol phosphatide and a drug, the drug being dissolved in the composition.

The glycerol phosphatide may be any one of the following compounds; phosphatidylcholine (lecithin), phosphatidylethanolamine (cephalin), phosphatidylinositol, phosphatidylserine, diphosphatidylglycerol or phosphatidic acid.

Surprisingly it has been found that glycerol phosphatides cause complete dissolution of certain drugs in chlorofluorocarbon propellents. Phosphatidylcholine (lecithin) has been utilised as a surfactant in aerosol formulations containing suspended drug particles but heretofore it has not been appreciated that this particular compound can enhance the solubility of certain drugs in chlorofluorocarbon propellents.

It has been found that drugs having at least very slight solubility in chlorofluorocarbon propellents will exhibit an enhanced solubility in the chlorofluorocarbon propellent in the presence of glycerol phosphatide. It is postulated that this enhanced solubility is attributable to drug in true solution becoming associated with reverse micelles of the glycerol phosphatide which allows further drug to dissolve in the propellent. Thus, the solubilisation process is believed to be as follows:

drug ⇌ drug in solution in propellent ⇌ drug associated with reverse micelles of glycerol phosphatide Initial solubilisation — Micellar solubilisation Whilst the compositions of the invention appear visibly to be true solutions since there is no dispersed phase apparent, they are more correctly micellar solutions.

The formulations of the invention may be prepared by forming a concentrate of glycerol phosphatide with a drug and Propellent 11. The concentrate may be formed by simple admixture with agitation and optionally under heating, e.g. 50° C., until complete dissolution of the drug has been attained. The concentrate may then be mixed with the remainder of the propellent formulation, e.g. Propellents 12 and 114.

Phosphatidylcholine is the most suitable glycerol phosphatide to use in view of its low toxicity and high drug solubilising efficacy. Phosphatidylcholine purified from soya bean lecithin is readily available commercially and suitable grades include Epikuron 200 (Lucas-Meyer) and Lipoid S100 (Lipoid KG). Both products have a phosphatidylcholine content in excess of 95%.

It has been found that certain drugs which are practically insoluble in chlorofluorocarbon propellents alone can be solubilised in the propellent/glycerol phosphatide system by the addition of a small amount of a co-solvent such as ethanol.

It is postulated that the co-solvent enhances the initial solubilisation step of the solubilisation process. Certain commercially available forms of lecithin, in addition to their phosphatidylcholine content, contain ethanol as an impurity. With compounds of this type, e.g. Lipoid S45, the ethanol may likewise enhance drug solubilisation.

Suitable drugs for use in the invention comprise those compounds which exhibit at least a very slight solubility in a chlorofluorocarbon propellent. In general, the drug will be in the form of an ester, base or free alcohol. Highly polar ionics salts of drugs are less suitable since it may not be possible to solubilise the drug in sufficient quantity even with the presence of a small amount of co-solvent.

Exemplary drugs include steroids, e.g. beclomethasone, dipropionate, betamethasone dipropionate, acetate, valerate and free alcohol. Other drugs include salbutamol base, atropine base, prednisolone, formoterol base, hydrochloride, fumarate and hemisulphate.

Further suitable drugs for use with the invention include the following:

Anorectics: e.g. benzphetamine hydrochloride, chlorphentermine hydrochloride
Anti-depressents: e.g. amitriptyline hydrochloride, imipramine hydrochloride
Anti-hypertensive agents: e.g. clonidine hydrochloride
Anti-neoplastic agents: e.g. actinomycin C
Anti-cholinergic agents: atropine base
Dopaminergic agents: e.g. bromocriptine mesylate
Narocotic analgestics: e.g. buprenorphine hydrochloride
Beta-adrenergic blocking agents: e.g. propranolol hydrochloride
Corticosteroids: e.g. lacicortone, hydrocortisone, fluocinolone acetonide, triamcinolone acetonide
Prostaglandins: e.g. dinoprost trometamol Sympathomimetics: e.g. xylometazoline hydrochloride
Tranquillisers: e.g. diazepam, lorazepam
Vitamins: e.g. folic acid, nicotinamide
Brocholdilators: e.g. clenbuterol hydrochloride bitolterol mesylate
Sex hormones: e.g. ethinyloestradiol, levonorgestrel.

The ratio of drug:glycerol phosphatide:cosolvent (if required): chloro-fluorocarbon propellent depends upon a number of criteria:
(1) The concentration of drug required in the final formulation.
(2) The solubility of glycerol phosphatide in the particular blend of chlorofluorocarbon propellents.
(3) The droplet size and evaporation characteristics required of the emitted spray. For inhalation purposes of optimum levels of glycerol phosphatide and Propellent 11 will be the minimum permissable levels to achieve a stable solution. Higher levels of these components result in an increase in the droplet size of the spray upon dispensing due to a lowering of the volatility of the formulation.
(4) Solubility of the drug in the propellents or propellent/co-solvent.

A wide range of propellents may be used in the formulations of the invention including:
Propellent 11 trichloromonofluoromethane
Propellent 12 dichlorodifluoromethane
Propellent 13 monochlorotrifluoromethane
Propellent 21 dichloromonofluoromethane
Propellent 22 monochlorodifluoromethane
Propellent 113 trichlorotrifluoroethane
Propellent 114 dichlorotetrafluoroethane
Propellent 115 monochloropentafluoroethane
Propellent 500 azetrope—73.8% dichlorodifluoromethane and 26.2% 1,1-difluoroethane In addition to chlorofluorocarbon aerosol propellent the formulations may contain other propellents, e.g. DME (dimethylether).

In general, the compositions comprising drug, glycerol phosphatide and propellent may be made within the following general weight ratios:
drug:glycerol phosphatide
1 to 500:100
glycerol phosphatide:propellent
0.01 to 20:100

For many drugs the weight ratio of drug:glycerol phosphatide will generally be in the range 1 to 30:100 and that of glycerol phosphatide:propellent in the range 0.01 to 10:100. Preferaly the weight ratio of drug:-glycerol phosphatide will be in the range 2 to 10:100 and that of glycerol phosphatide:propellent in the range 0.01 to 3:100.

The invention will now be illustrated by the following Examples.

EXAMPLE 1

Solubilisation of beclomethasone dipropionate

|     |                            | mg/ml |
| --- | -------------------------- | ----- |
| (a) | beclomethasone dipropionate | 1    |
| (b) | Epikuron 200               | 14    |
| (c) | Propellent 11              | 270   |
| (d) | Propellent 12              | 1080  |
|     |                            | 1365  |

The formulation was prepared by mixing components (a) to (c) under stirring for approximately 10 minutes at a temperature of 25° C. Thereafter the concentrate was mixed with component (d) at a temperature appropriate to the filling technique, generally in the range −60° to +20° C. The resulting formulation was a stable solution.

EXAMPLE 2

Solubilisation of salbutamol base

|     |                 | mg/ml |
| --- | --------------- | ----- |
| (a) | salbutamol base | 2     |
| (b) | Epikuron 200    | 14    |
| (c) | Propellent 11   | 339   |
| (d) | Propellent 12   | 1018  |
|     |                 | 1373  |

The formulation was prepared as in Example 1 except that solubilisation required stirring for 30 minutes at a temperature of 50° C. A stable solution was formed.

EXAMPLE 3

Solubilisation of atropine base

|     |               | mg/ml |
| --- | ------------- | ----- |
| (a) | atropine base | 1     |
| (b) | Epikuron 200  | 4     |
| (c) | Propellent 11 | 270   |
| (d) | Propellent 12 | 1080  |
|     |               | 1355  |

The formulation was prepared as in Example 1 and resulted in a stable solution.

EXAMPLE 4

A series of stable formulations were prepared suitable for use as concentrates in the preparation of aerosol formulations. Each concentrate comprised the following components in the weight ratio of drug:Epikuron 200:Propellent 11 of 1:14:270. The drugs used were prednisolone, betamethasone acetate, betamethasone valerate, betamethasone dipropionate and betamethasone free alcohol.

EXAMPLE 5

Solubilisation of formoterol compounds

The following formulations were prepared:

|       |                          | mg/ml      |
| ----- | ------------------------ | ---------- |
| (i)   | formoterol hydrochloride | 0.2000     |
|       | ascorbyl palmitate       | 0.2000     |
|       | Epikuron 200             | 2.7000     |
|       | Propellent 11            | 341.4125   |
|       | Propellent 12            | 1024.2375  |
|       |                          | 1368.7500  |
| (ii)  | formoterol hydrochloride | 0.2400     |
|       | vitamin E acetate        | 2.7000     |
|       | Epikuron 200             | 2.7000     |
|       | Propellent 11            | 339.8400   |
|       | Propellent 12            | 1019.5200  |
|       |                          | 1365.0000  |
| (iii) | formoterol hydrochloride | 0.1800     |
|       | Lipoid S45 Lecithin      | 2.7000     |
|       | Propellent 11            | 202.0680   |
|       | Propellent 12            | 1145.0520  |
|       |                          | 1350.0000  |
| (iv)  | formoterol base          | 0.1600     |
|       | Lipoid S45 Lecithin      | 2.7000     |
|       | Propellent 11            | 202.0710   |
|       | Propellent 12            | 1145.0690  |

|     |                      | mg/ml     |
| --- | -------------------- | --------- |
|     |                      | 1350.0000 |
| (v) | formoterol hemisulphate | 0.1600 |
|     | Lipoid S45 Lecithin  | 2.7000    |
|     | Propellent 11        | 202.0710  |
|     | Propellent 12        | 1145.0690 |
|     |                      | 1350.0000 |
| (vi)| formoterol fumarate  | 0.2400    |
|     | vitamin E acetate    | 2.7000    |
|     | Epikuron 200         | 2.7000    |
|     | Propellent 11        | 339.8400  |
|     | Propellent 12        | 1019.5200 |
|     |                      | 1365.0000 |
|(vii)| formoterol fumarate  | 0.2400    |
|     | Epikuron 200         | 2.7000    |
|     | Propellent 11        | 340.5150  |
|     | Propellent 12        | 1021.5450 |
|     |                      | 1365.0000 |

Vitamin E acetate and ascorbyl palmitate were included as antioxidants and did not impair the physical characteristics of the solutions.

The formulations were prepared by mixing the drug, surfacant, Propellent 11 and antioxidant (when present) under stirring for up to 6 hours at a temperature of 45° to 50° C. Thereafter the resulting solution was mixed with Propellent 12 at a temperature appropriate to the filling method to produce a solution.

EXAMPLE 6

A series of stable formulations were prepared suitable for use as concentrates in the preparation of aerosol formulations. Each concentrate comprised drug, Lipoid S100 and Propellent 11 in the weight ratio of 1:7:135. The drugs used were:
Diazepam
Lorazepam
propranolol hydrochloride
hydrocortisone
fluocinolone acetonide
triamcinolone acetonide
Clear stable solutions resulted in all cases. When matching formulations were prepared omitting Lipoid S100 each drug remained in suspension.

EXAMPLE 7

Use of co-solvent to aid solubilisation

A formulation was prepared consisting of xylometazoline hydrochloride, Lipoid S100 and Propellent 11 in the weight ratio 1:7:135. A matching formulation was prepared in which the Lipoid S100 was omitted. After agitation and heating at 50° C. for four hours a considerable amount of drug remained in suspension, in both formulations. Ethanol 4% by weight was then added to both formulations. After 15 minutes the formulation containing Lipoid S100 was a clear solution. There was no apparent change in the formulation in which Lipoid S100 was omitted. This result indicates the efficiency of a small amount of co-solvent in promoting the initial solubilisation step of the phospholipid solubilisation process.

EXAMPLE 8

Aerosol formulations containing Diazepam

The following formulations were prepared:

|     |               | mg/ml  |      |
| --- | ------------- | ------ | ---- |
| (a) | Diazepam      | 20     |      |
|     | Lipoid S100   | 7      |      |
|     | Propellent 11 | 370.5  | 30%  |
|     | Propellent 12 | 864.5  | 70%  |
|     |               | 1262.0 |      |
| (b) | Diazepam      | 20     |      |
|     | Lipoid S100   | 7      |      |
|     | Propellent 11 | 264.3  | 30%  |
|     | DME           | 616.7  | 70%  |
|     |               | 908.0  |      |

The formulations were physically stable solutions.

EXAMPLE 9

Use of Propellents 113 and 115 in solubilised formulations

The following formulation was prepared:

|               | mg/ml   |
| ------------- | ------- |
| Lorazepam     | 1.87    |
| Lipoid S100   | 13.09   |
| Propellent 113| 252.59  |
| Propellent 115| 126.29  |
| Propellent 22 | 884.06  |
|               | 1277.90 |

Dissolution of the concentrate containing Lorazepam, Lipoid S100 and Propellent 113 was achieved by heating at 50° C. for 10 minutes. Propellent 115 and Propellent 22 were then combined with the concentrate and a physically stable solution resulted.

EXAMPLE 10

Use of Propellent 500 (Azeotrope) in solubilised formulation

The following formulation was prepared:

|               | mg/ml   |
| ------------- | ------- |
| Propranolol HCl | 3.02  |
| Lipoid S100   | 21.14   |
| Propellent 11 | 407.65  |
| Propellent 500| 951.19  |
|               | 1383.00 |

A physically stable solution formulation resulted.

EXAMPLE 11

Solubilisation of bitolterol mesylate

The following formulations were prepared:

|                    | mg/ml   | mg/ml   |
| ------------------ | ------- | ------- |
| bitolterol mesylate | 4.00   | 8.00    |
| Lipoid S100        | 10.00   | 20.00   |
| Propellent 11      | 201.30  | 199.20  |
| Propellent 12      | 1140.70 | 1128.80 |
|                    | 1356.00 | 1356.00 |

Solubilisation occurred readily in the Propellent 11/lecithin/drug concentrates at room temperature. Both solution formulations were stable at −60° C. enabling the cold filling technique to be employed when preparing pressurised dispensing packs.

EXAMPLE 12

Solubilisation of Lacicortone

The following formulations were prepared:

|  | (a) mg/ml | (b) mg/ml |
|---|---|---|
| Lacicortone | 2.00 | 5.00 |
| Lipoid S100 | 7.00 | 14.00 |
| Propellent 11 | 271.20 | 408.60 |
| Propellent 12 | 1084.80 | 953.40 |
|  | 1365.00 | 1381.00 |

Solubilisation occurred readily in the Propellent 11/lecithin/drug concentrates at room temperature. Formulation (a) was stable at −60° C. and Formulation (b) was stable at −50° C. enabling the cold filling technique to be employed when preparing pressurised dispensing packs.

EXAMPLE 13

Use of glycerol phosphatides

The following formulations were prepared:

|  | parts by weight |
|---|---|
| beclomethasone dipropionate | 1 |
| phosphatidyl serine | 14 |
| Propellent 11 | 270 |
| beclomethasone dipropionate | 1 |
| phosphatidyl ethanolamine | 14 |
| Propellent 11 | 270 |
| salbutamol base | 1 |
| phosphatidyl serine | 14 |
| Propellent 11 | 270 |
| salbutamol base | 1 |
| phosphatidyl ethanolamine | 14 |
| Propellent 11 | 270 |

Each formulation was a stable clear solution suitable for use as a concentrate in the preparation of aerosol formulations.

We claim:

1. An aerosol formulation comprising one or more chlorofluorocarbon aerosol propellants, a glycerol phosphatide and a solubilized drug, substantially all of the drug being dissolved in the composition, and which drug is substantially insoluble in the propellant absent the glycerol phosphatide.

2. A formulation as claimed in claim 1, in which the glycerol phosphatide is selected from phosphatidylcholine, phosphatidylethanolamine, phosphatidylinositol, phosphatidylserine, diphosphatidylglycerol, phosphatidic acid and mixtures thereof.

3. A formulation as claimed in claim 2, in which the glycerol phosphatide is phosphatidylcholine.

4. A formulation as claimed in claim 1, in which the glycerol phosphatide is purified.

5. A formulation as claimed in claim 1, which comprises Propellant 11, glycerol phosphatide and a drug.

6. A formulation as claimed in claim 1, which additionally comprises a small amount of a co-solvent to enhance the solubilisation process.

7. A formulation as claimed in claim 1, in which the drug is selected from beclomethasone dipropionate, betamethasone dipropionate, acetate, valerate and base thereof, salbutamol base, atropine base and prednisolone.

8. A formulation as claimed in claim 1, in which the drug is selected from formoterol base, hydrochloride, hemisulphate and fumarate.

9. A formulation as claimed in claim 1, in which the drug is selected from diazepam, lorazepam, propranolol hydrochloride, hydrocortisone, fluocinolone acetonide, triamcinolone acetonide, xylometazoline hydrochloride, bitolterol mesylate and lacicortone.

10. A pressurised aerosol pack filled with a formulation as claimed in claim 1.

11. A method of solubilising a drug having slight solubility in chlorofluorocarbon aerosol propellents which comprises mixing said drug in a chlorofluorocarbon propellent in the presence of an effective amount of a glycerol phosphatide.

12. A method as claimed in claim 11, which additionally comprises the addition of a small amount of a co-solvent to enhance the solubilisation process.

13. A method as claimed in claim 11, in which the drug is selected from beclomethasone dipropionate, betamethasone dipropionate, acetate, valerate and base thereof, salbutamol base, atropine base, and prednisolone.

14. A method as claimed in claim 11, in which the drug is selected from formoterol base, hydrochloride, hemisulphate and fumarate.

15. A method as claimed in claim 11, in which the drug is selected from diazepam, lorazepam, propranolol hydrochloride, hydrocorisone, fluocinolone acetonide, triamcinolone acetonide, xylometazoline hydrochloride, bitolterol mesylate and lacicortone.

16. A process for solubilising a drug having slight solubility in chlorofluorocarbon aerosol propellent which comprises using an effective amount of glycerol phosphatide.

* * * * *